(12) United States Patent
Baynes

(10) Patent No.: US 6,966,320 B1
(45) Date of Patent: Nov. 22, 2005

(54) SURGICAL COVERING ASSEMBLY

(76) Inventor: Samentha Baynes, 87 Central Park La., Powder Springs, GA (US) 30127

( * ) Notice: Subject to any disclaimer, the term of this patent is extended or adjusted under 35 U.S.C. 154(b) by 0 days.

(21) Appl. No.: 10/984,228

(22) Filed: Nov. 9, 2004

(51) Int. Cl.[7] .............................................. A61B 19/08
(52) U.S. Cl. ...................... 128/853; 128/849; 128/850; 128/853; 128/855
(58) Field of Search ................................. 128/849, 850, 128/851, 852, 853, 854, 855, 856; 602/42, 602/41, 43, 52, 54, 57

(56) References Cited

U.S. PATENT DOCUMENTS

| 2,273,873 | A | * | 2/1942 | Klein | 128/888 |
| D256,161 | S | | 7/1980 | Oliver | |
| 4,476,860 | A | | 10/1984 | Collins et al. | |
| 4,505,770 | A | * | 3/1985 | Larimore | 156/235 |
| 4,664,103 | A | | 5/1987 | Martin et al. | |
| 4,917,112 | A | * | 4/1990 | Kalt | 602/58 |
| 5,086,763 | A | * | 2/1992 | Hathman | 602/42 |
| 5,178,162 | A | * | 1/1993 | Bose | 128/849 |
| 5,197,493 | A | * | 3/1993 | Grier-Idris | 128/853 |
| 5,275,177 | A | * | 1/1994 | Wilk | 128/849 |
| 5,562,107 | A | * | 10/1996 | Lavender et al. | 128/888 |
| 5,702,356 | A | * | 12/1997 | Hathman | 602/41 |
| 5,860,420 | A | | 1/1999 | Wiedner et al. | |
| 6,297,420 | B1 | * | 10/2001 | Heincke | 602/41 |
| 2002/0020418 | A1 | | 2/2002 | Lofgren | |
| 2002/0108615 | A1 | | 8/2002 | Levitt et al. | |

* cited by examiner

*Primary Examiner*—Henry Bennett
*Assistant Examiner*—Camtu Nguyen
(74) *Attorney, Agent, or Firm*—The Hope Law Firm, LLC

(57) ABSTRACT

A surgical covering assembly includes a flexible cover that has a length and width each greater than 2.30 feet. The cover has an opening extending therethrough. A transparent window is attached to the cover and substantially covers the opening. The window comprises a flexible material that has at least one section therein defined by perforation lines to allow the selective removal of the section from the window. The section may be selectively removed from the window. The cover may be positioned over a body such that window is aligned with an area to be operated on.

14 Claims, 4 Drawing Sheets

SURGICAL COVERING ASSEMBLY

BACKGROUND OF THE INVENTION

1. Field of the Invention

The present invention relates to surgical covering devices and more particularly pertains to a new surgical covering device for providing a convenient opening through a surgical sheet.

2. Description of the Prior Art

The use of surgical covering devices is known in the prior art. U.S. Pat. No. 5,860,420 describes a two part surgical draping system having both reusable and disposable portions. Another type of surgical covering device is U.S. Pat. No. 4,664,103 having a particular design adapted for cardiovascular procedures. Yet another such device is U.S. Pat. No. 4,476,860 which includes a surgical drape having pockets therein for holding a plurality of medical instruments.

While these devices fulfill their respective, particular objectives and requirements, the need remains for a device that includes an opening therein with a window having a plurality of removable sections therein so that a surgeon may selectively decide the size of the opening in the surgical drape. What is also needed is a towel system that adheres to the patient and are attachable to adjacent towels positioned on the patient in such a way the surgical area is framed by the towels.

SUMMARY OF THE INVENTION

The present invention meets the needs presented above by generally comprising a flexible cover that has a length and width each greater than 2.30 feet. The cover has an opening extending therethrough. A transparent window is attached to the cover and substantially covers the opening. The window comprises a flexible material that has at least one section therein defined by perforation lines to allow the selective removal of the section from the window. The section may be selectively removed from the window. The cover may be positioned over a body such that window is aligned with an area to be operated on.

The invention is also found in towels having adhesive means thereon for attaching the towels to the body. The towels also include couplers for attaching the towels together as they are positioned on the patient.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
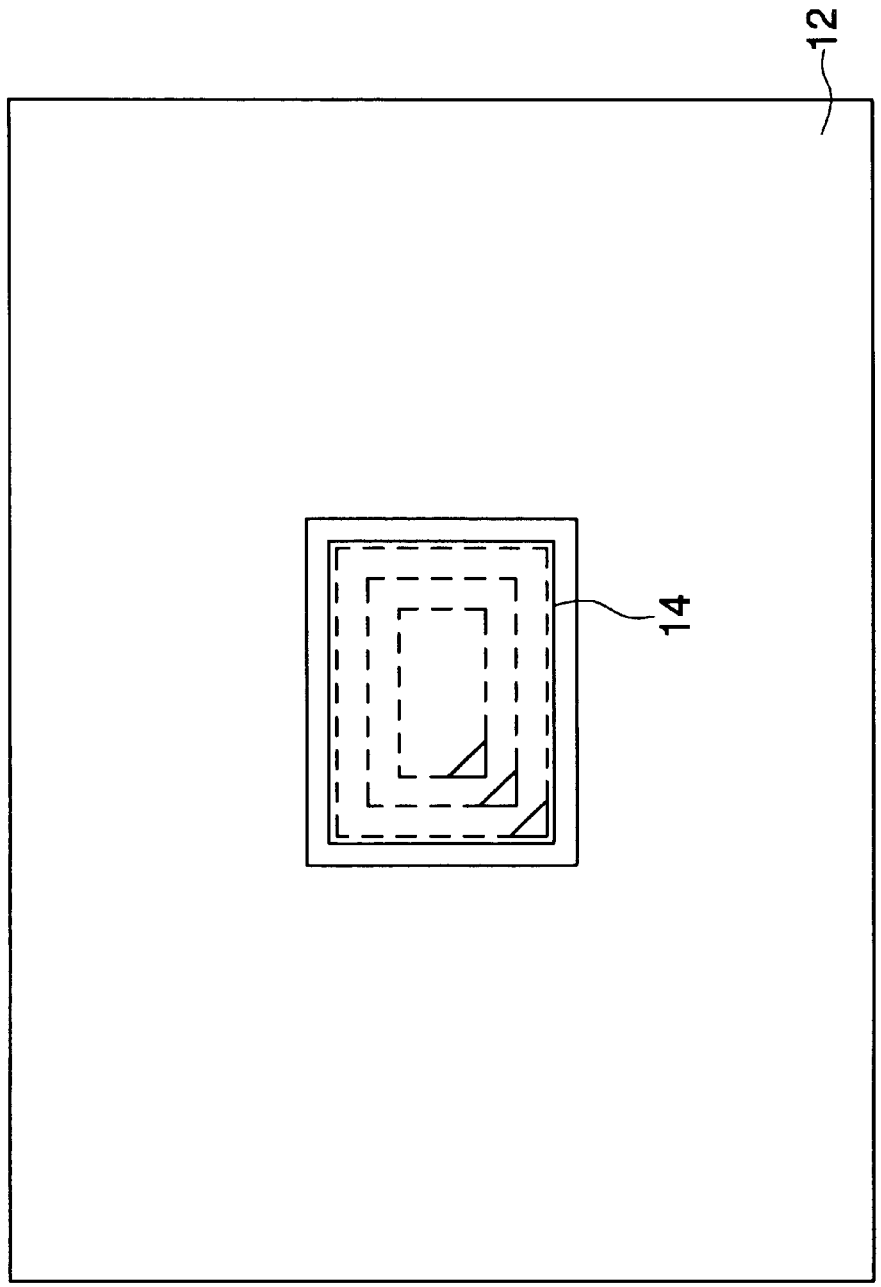
FIG. 1 is a top view of a surgical covering assembly according to the present invention.
Figure 2:
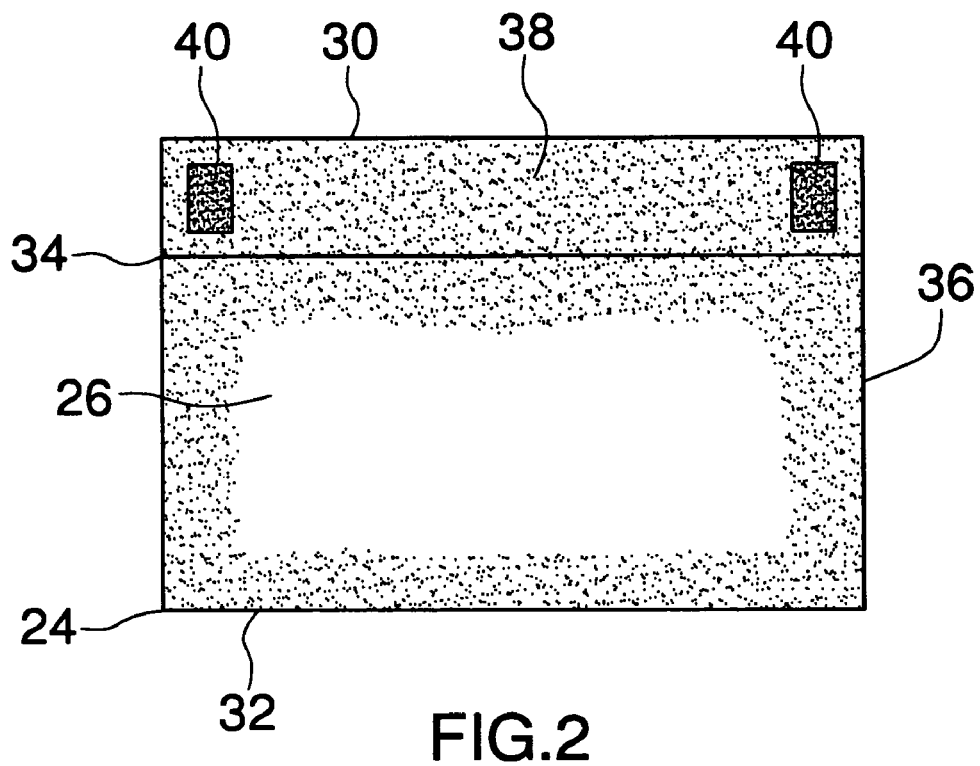
FIG. 2 is a first side view of a towel of the present invention.
Figure 3:
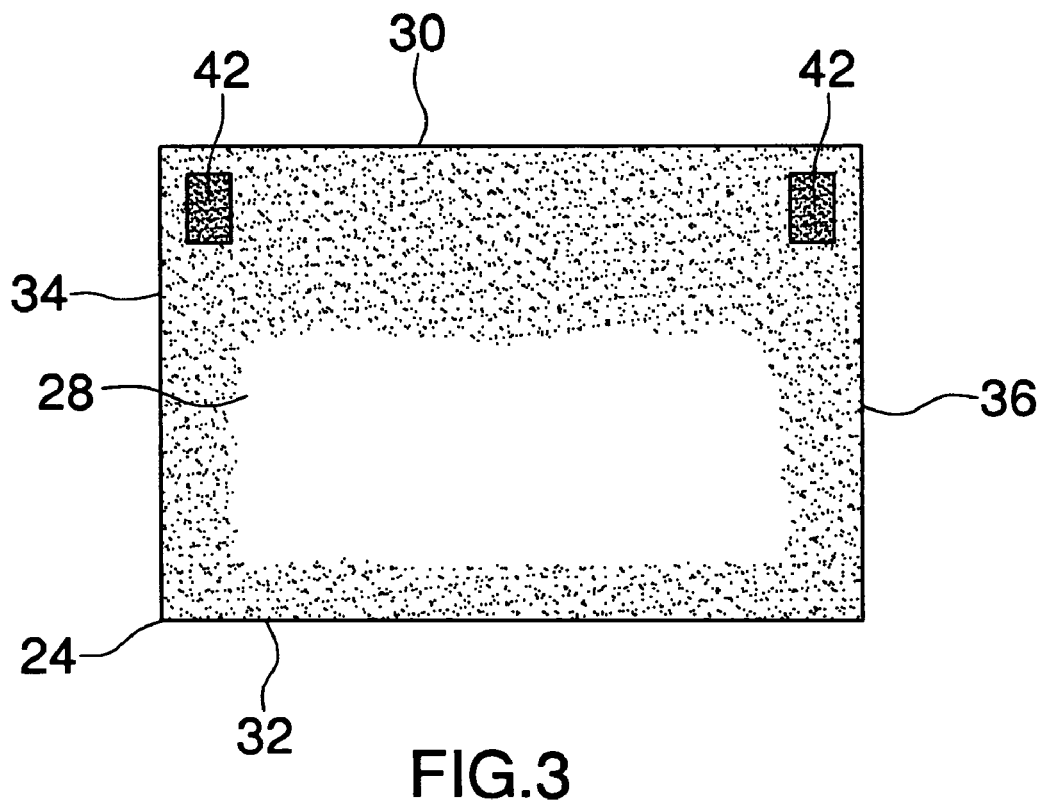
FIG. 3 is a second side view of a towel of the present invention.
Figure 4:
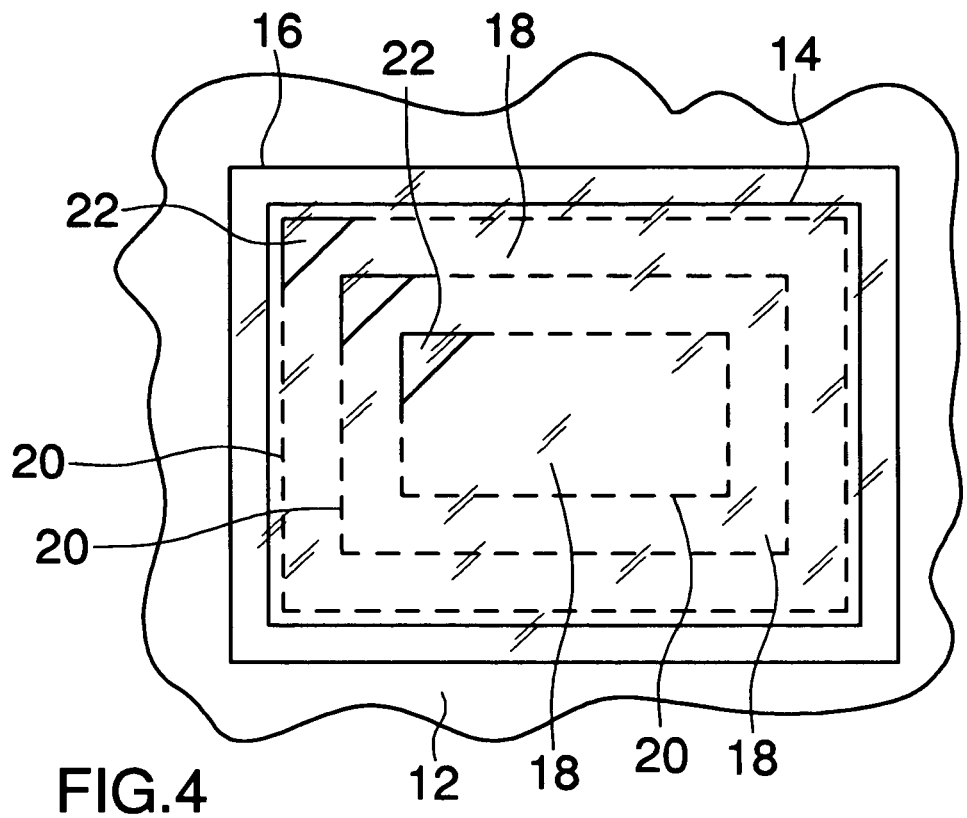
FIG. 4 is an enlarged view of a window of the present invention.
Figure 5:
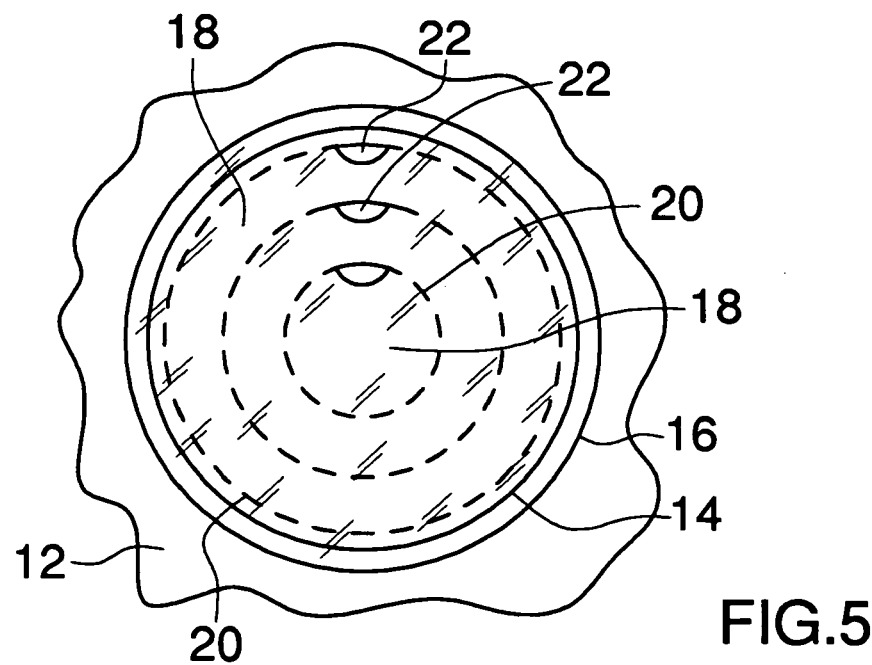
FIG. 5 is an enlarged view of the window of the present invention.

With reference now to the drawings, and in particular to FIGS. 1 through 7 thereof, a new surgical covering device embodying the principles and concepts of the present invention and generally designated by the reference numeral 10 will be described.

As best illustrated in FIGS. 1 through 7, the surgical covering assembly 10 generally includes a flexible cover 12 that has a length and width each greater than 2.30 feet. The cover 12 is comprised of conventional surgical drape cloth material that is typically utilized for surgical sheets. This material generally includes cotton, polyester and combinations thereof. The cover 12 has an opening 14 extending therethrough that is generally centrally located on the cover. The opening 14 has an area of generally between 15 square inches and 80 square inches. The opening 14 may either have a substantially rectangular shape or a substantially circular shape. It should be understood that the cover 12 might include arm covers, not shown, attached thereto which are often used with surgical drapes to ensure that a patient's arms are also covered.

A transparent window 16 is attached to the cover and substantially covering the opening. The window 16 comprises a flexible material preferably comprised of a plastic material. The window 16 has at least one and preferably a plurality of concentric sections 18 therein each defined by perforation lines 20. The perforation lines 20 are comprised of perforations extending through the window 16. The perforation lines 20 allow the sections 18 to be selectively removed from the window 16. The sections 18 may be either circular shaped or rectangular shaped. The plurality of concentric sections 18 is preferably at least three sections 18. Each of a plurality of gripping tabs 22 is attached to one of the sections 18. The tabs 22 are preferably positioned adjacent to the perforations. By pulling the tab 22, the sections 18 may be removed so that a surgeon may reach through the window 16 and the opening 14.

A plurality of towels 24 is preferably included with the cover 12 to form a surgery kit. The towels 24 may be comprised of a cloth material. Each of the towels 24 has a first side 26, a second side 28, a first edge 30, a second edge 32, a third edge 34 and a fourth edge 36. The first 30 and second 32 edges are positioned opposite of each other. Each of a plurality of pressure adhesive strips 38 is attached to one if the first sides 26 of the towels 24. Each of the strips 38 extends along an associated one of the first edges 30.

Figure 6:
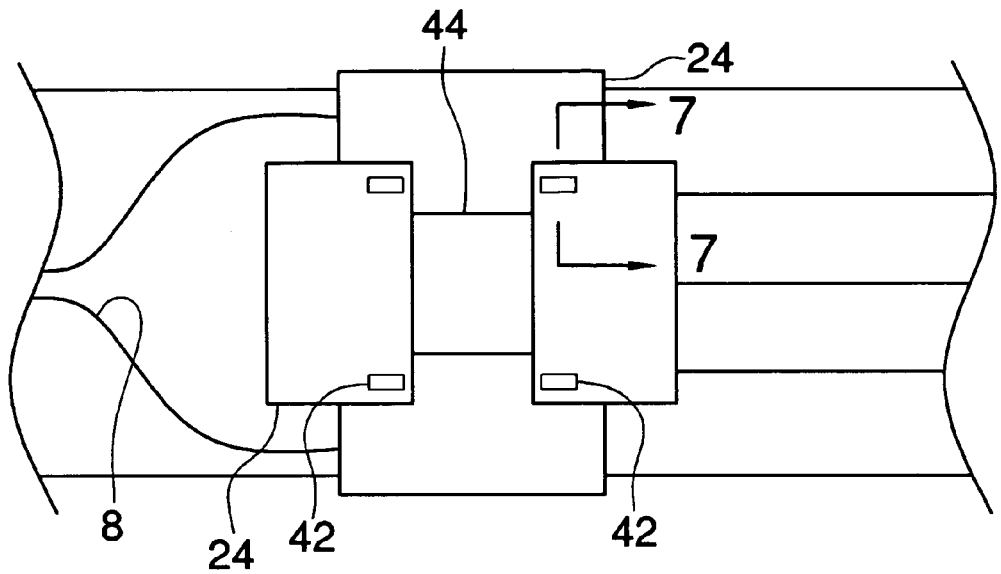
FIG. 6 is an in-use view of the towels of the present invention.
Figure 7:
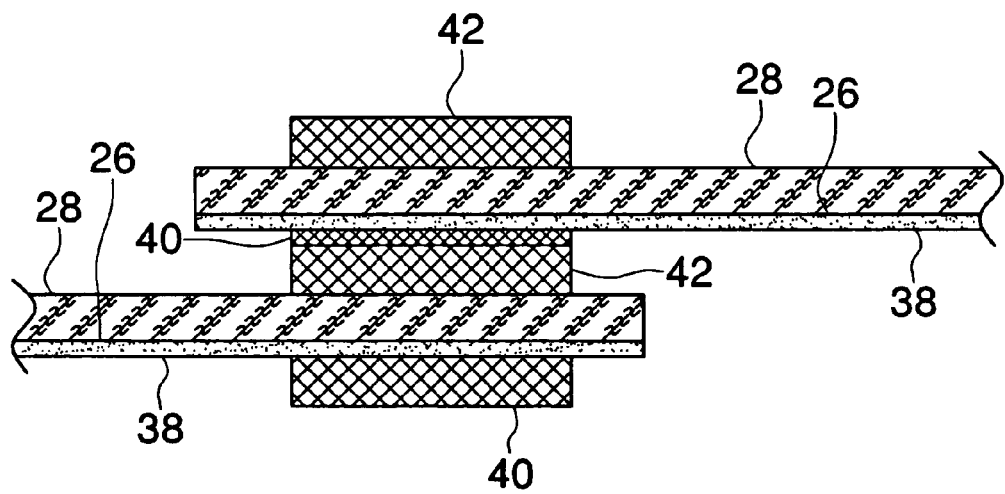
FIG. 7 is a cross-sectional view taken along line 7—7 of FIG. 6 of the present invention.

A plurality of couplers is included for selectively attaching the towels 24 together at their corners. Each of the couplers includes a first engaging member 40 and a second engaging member 42. The first 40 and second 42 engaging members are adapted for removably engaging each other. Each of the first sides 26 of the towels 24 has a pair of first engaging members 40 attached thereto that are positioned adjacent to the first side edge 30. The first engaging members 40 on each of the towels 24 are spaced from each other such that each of the first engaging members 40 is positioned adjacent to one of the third 34 and fourth 36 side edges. Each of the second sides 28 of the towels 24 has a pair of second engaging members 42 attached thereto that are positioned adjacent to the first side edge 30. The second engaging members 42 on each of the towels 24 are spaced from each other such that each of the second engaging members 42 is positioned adjacent to one of the third 34 and fourth 36 side edges. The towels 24 may be overlapped as shown in FIG. 6 such that the first 40 and second 42 engaging members removably engage each other and thereby removably secure the corners together. Each of the couplers preferably includes a hook and loop securing means.

In use, the towels 24 may be attached to a body with the adhesive strips 38 and orientated such that an aperture 44 is defined between spaced ones of the towels 24. The aperture 44 is aligned with an area on a patient 8 to be operated on. The couplers may be used for selectively coupling together adjacent ones of the towels 24 to prevent their movement with respect to each other. The cover 12 is first selected that has the appropriately shaped opening 14 for the surgery to be performed. Thus, a rounded shape may be utilized for operations on children or for mastectomies while the rectangular shapes may be used for other operations. The cover 12 is positioned over the towels 24 such that the window 16 is aligned with the aperture 44. The sections 18 of the needed size are removed along the perforation lines 20 so that a surgeon can reach through the window 16 to perform the operation.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A surgery covering assembly comprising:
   a flexible cover having a length and width each greater than 2.30 feet, said cover having an opening extending therethrough;
   a transparent window being attached to said cover and substantially covering said opening, said window comprising a flexible material, said window having at least one section therein defined by perforation lines, said section being selectively removable from said window along said perforation lines; and
   wherein the cover may be positioned over a body such that window is aligned with an area to be operated on.

2. The assembly according to claim 1, wherein said opening is generally centrally located on said cover.

3. The assembly according to claim 1, wherein said opening has an area of generally between 15 square inches and 80 square inches.

4. The assembly according to claim 3, wherein said opening has a substantially rectangular shape.

5. The assembly according to claim 3, wherein said opening has a substantially circular shape.

6. The assembly according to claim 1, wherein said at least one section includes at least three concentric sections each being defined by perforation lines.

7. The assembly according to claim 1, at least one gripping tab being attached to said at least one section.

8. The assembly according to claim 6, further including a plurality of gripping tabs, each of said gripping tabs being attached to one of said sections.

9. The assembly according to claim 1, further including a plurality of towels, each of said towels having a first side, a second side, a first edge, a second edge, a third edge and a fourth edge, said first and second edges being positioned opposite of each other, a plurality of pressure adhesive strips, each of said strips being attached to one of said first sides of said towels, each of said strips extending along an associated one of said first edges, wherein the towels may be positioned under the cover and attached to the body with said adhesive strips and orientated such that an aperture is defined between spaced ones of said towels, the aperture being aligned with the opening in the cover.

10. The assembly according to claim 9, a plurality of couplers, each of said couplers including a first engaging member and a second engaging member adapted for removably engaging each other, each of said first sides of said towels having a pair of first engaging members attached thereto and being positioned adjacent to said first side edge, said first engaging members on each of said towels being spaced from each other such that each of said first engaging members is positioned adjacent to one of said third and fourth side edges, each of said second sides of said towels having a pair of second engaging members attached thereto and being positioned adjacent to said first side edge, said second engaging members on each of said towels being spaced from each other such that each of said second engaging members is positioned adjacent to one of said third and fourth side edges, wherein said towels may be overlapped with each other such that said first and second engaging members removably engage each other.

11. The assembly according to claim 6, further including a plurality of towels, each of said towels having a first side, a second side, a first edge, a second edge, a third edge and a fourth edge, said first and second edges being positioned opposite of each other, a plurality of pressure adhesive strips, each of said strips being attached to one of said first sides of said towels, each of said strips extending along an associated one of said first edges, wherein the towels may be positioned under the cover and attached to the body with said adhesive strips and orientated such that an aperture is defined between spaced ones of said towels, the aperture being aligned with the opening in the cover.

12. The assembly according to claim 11, a plurality of couplers, each of said couplers including a first engaging member and a second engaging member adapted for removably engaging each other, each of said first sides of said towels having a pair of first engaging members attached thereto and being positioned adjacent to said first side edge, said first engaging members on each of said towels being spaced from each other such that each of said first engaging members is positioned adjacent to one of said third and fourth side edges, each of said second sides of said towels having a pair of second engaging members attached thereto and being positioned adjacent to said first side edge, said second engaging members on each of said towels being spaced from each other such that each of said second engaging members is positioned adjacent to one of said third and fourth side edges, wherein said towels may be overlapped with each other such that said first and second engaging members removably engage each other.

13. The assembly according to claim 12, further including a plurality of gripping tabs, each of said gripping tabs being attached to one of said sections.

14. A surgery covering assembly comprising:
- a flexible cover having a length and width each greater than 2.30 feet, said cover having an opening extending therethrough, said opening being generally centrally located on said cover, said opening having an area of generally between 15 square inches and 80 square inches, said opening having a substantially rectangular shape;
- a transparent window being attached to said cover and substantially covering said opening, said window comprising a flexible material, said window having a plurality of concentric sections therein defined by perforation lines, wherein said sections may be selectively removed from said window, said plurality of concentric sections being at least three sections;
- a plurality of gripping tabs, each of said gripping tabs being attached to one of said sections;
- a plurality of towels, each of said towels having a first side, a second side, a first edge, a second edge, a third edge and a fourth edge, said first and second edges being positioned opposite of each other;
- a plurality of pressure adhesive strips, each of said strips being attached to one of said first sides of said towels, each of said strips extending along an associated one of said first edges;
- a plurality of couplers, each of said couplers including a first engaging member and a second engaging member adapted for removably engaging each other, each of said first sides of said towels having a pair of first engaging members attached thereto and being positioned adjacent to said first side edge, said first engaging members on each of said towels being spaced from each other such that each of said first engaging members is positioned adjacent to one of said third and fourth side edges, each of said second sides of said towels having a pair of second engaging members attached thereto and being positioned adjacent to said first side edge, said second engaging members on each of said towels being spaced from each other such that each of said second engaging members is positioned adjacent to one of said third and fourth side edges, wherein said towels may be overlapped such that said first and second engaging members removably engage each other, each of said couplers including a hook and loop securing means; and
- wherein the towels may be attached to a body with said adhesive strips and orientated such that an aperture is defined between spaced ones of said towels, the aperture being alignable with an area to be operated on, wherein said couplers selectively couple adjacent ones of said towels, and wherein the cover may be positioned over the towels such that the window is aligned with the aperture.

* * * * *